(12) United States Patent
White

(10) Patent No.: US 7,273,585 B1
(45) Date of Patent: Sep. 25, 2007

(54) BIOLOGICAL FLUID DISPOSAL SYSTEM

(76) Inventor: James M. White, P.O. Box 3462, Longview, TX (US) 75606

( * ) Notice: Subject to any disclaimer, the term of this patent is extended or adjusted under 35 U.S.C. 154(b) by 1128 days.

(21) Appl. No.: 09/596,370

(22) Filed: Jun. 19, 2000

(51) Int. Cl.
  *A61L 9/00* (2006.01)
  *A61L 2/00* (2006.01)
  *B01D 11/04* (2006.01)
  *C02F 1/76* (2006.01)
  *B01F 15/00* (2006.01)

(52) U.S. Cl. ............... 422/28; 422/1; 422/32; 422/256; 422/261; 422/292; 422/905; 210/198.1; 210/199; 210/752; 210/753; 210/754; 210/755; 210/756; 366/163.1; 366/163.2; 366/417

(58) Field of Classification Search ............ 422/1, 422/28, 32–33, 37, 256, 261, 292, 300, 905; 210/198.1, 199, 752–756; 366/163.1–163.2, 366/417, 199; 137/889–897, 888
See application file for complete search history.

(56) References Cited

U.S. PATENT DOCUMENTS

| 3,857,409 A | * | 12/1974 | Aubrey et al. ............... 137/412 |
| 3,975,271 A | * | 8/1976 | Saunier et al. ............... 210/754 |
| 3,975,284 A | * | 8/1976 | Lambert ................. 252/187.22 |
| 4,247,531 A | * | 1/1981 | Hicks .......................... 423/477 |
| 4,590,057 A | * | 5/1986 | Hicks .......................... 423/477 |
| 4,863,446 A | | 9/1989 | Parker |
| 4,957,491 A | | 9/1990 | Parker |
| 5,087,420 A | * | 2/1992 | Jackson ........................ 422/37 |
| 5,242,434 A | | 9/1993 | Terry |
| 5,387,204 A | | 2/1995 | Olsson et al. |
| 5,741,238 A | | 4/1998 | Bradbury et al. |
| 5,776,118 A | | 7/1998 | Seifert et al. |
| 5,885,240 A | | 3/1999 | Bradbury et al. |
| 5,914,047 A | * | 6/1999 | Griffiths ...................... 210/739 |
| 6,000,418 A | * | 12/1999 | Kern et al. ..................... 137/7 |

* cited by examiner

*Primary Examiner*—Gladys J P Corcoran
*Assistant Examiner*—Monzer R. Chorbaji
(74) *Attorney, Agent, or Firm*—Egbert Law Offices

(57) ABSTRACT

A biological fluid disposal system having a water flow line, a biological fluid line in fluid communication with the water flow line, a disinfectant line in fluid communication with the water flow line and the biological fluid line, and a venturi connected to one of the lines for creating a suction force so as to draw a biological fluid and a disinfectant in mixed relationship through the water flow line. The venturi includes a source of water pressure connected to the water flow line such that the water flow across an opening of either the biological fluid line and disinfectant line creates the suction force. The disinfectant line is connected to the biological fluid line between the water flow line and source of biological fluid.

15 Claims, 2 Drawing Sheets

BIOLOGICAL FLUID DISPOSAL SYSTEM

BACKGROUND OF THE INVENTION

1. Field of the Invention

The present invention relates to apparatus and methods for the disposal of waste biological fluids. More particularly, the present invention relates to the disposal of blood by mixing the blood with a disinfectant prior to passing to a sewer.

2. Description of Related Art

Over the years, hospitals and other healthcare facilities have been searching for a safe and convenient manner in which to handle and dispose of fluids aspirated from patients during surgical procedures. A major concern today is to reduce the hospital personnel's exposure to the fluids which may contain harmful and dangerous substances.

There are various means for collecting and handling waste materials, including bodily fluids that are aspirated during surgical operation or accumulated for some other reason where a patient is located. Waste materials and body fluids that can be collected include blood, urine, mucus and other bodily discharges. Known waste collection devices and systems include various types of containers into which the collected waste materials are accumulated during surgery and otherwise and from which they are dispensed or poured and sometimes disinfected at a later time. Such devices are usually removed from the place where the collection is made and while the waste materials are still contaminated. If decontamination is to take place before waste disposal, they are decontaminated or disinfected at some other location remote from where they are collected and before discharge into a larger waste receptacle or into a waste disposal system or sewer.

In the past, various U.S. patents have issued relating to such biological fluid disposal systems. For example, U.S. Pat. No. 4,863,446, issued on Sep. 5, 1989 to R. D. Parker, teaches a combination fluid collection and disposal apparatus. This apparatus includes a collection unit for collecting the fluid in a treatment unit for coupling with the collection unit to remove the fluid from the collection unit and to dispose the fluid. The collection unit is a reservoir for the temporary storage of fluids aspirated from the patient, a vacuum port for connecting the collection unit to a vacuum source and vacuum line connected to the vacuum port to the reservoir. U.S. Pat. No. 4,957,491, issued on Sep. 18, 1990 to the same inventor, describes a similar apparatus.

U.S. Pat. No. 5,087,420, issued on Feb. 11, 1992 to E. E. Jackson, describes a disposal system for infectious waste where the waste is drawn into a container. At the same time, a disinfectant is drawn into the container. The disinfectant and the infectious waste are mixed in the chamber before being forwarded to a drain or for disposal. An aspirator pump creates the requisite vacuum. The device also utilizes a macerator for the purpose of fragmenting the biological components prior to disposal.

U.S. Pat. No. 5,242,434, issued on Sep. 7, 1993 to W. M. Terry, teaches another medical waste handling system in which the infectious fluid is mixed with a disinfectant from another container before being discharged into the environment. Various conduits are connected to a collection chamber. Various other types of pumps are employed so as to introduce or to release fluid from the collection chamber.

U.S. Pat. No. 5,387,204, issued on Feb. 7, 1995 to Olsson et al., describes an apparatus and method for dosing an additive at the collection of liquid. The apparatus uses a suction to draw contaminated fluid through a tube. While the contaminated fluid is passed through a tube, it is mixed with a disinfectant before being forwarded for discharge.

U.S. Pat. No. 5,741,238, issued on Apr. 21, 1998 to Bradbury et al., teaches a medical and biological fluid collection and disposal system in which a vessel is divided into compartments which receive the biological fluid wastes through an inlet fitting. As the fluid is received, air in the vessel is displaced and is discharged through a vent line. When a level sensor senses that a level of fluid in the vessel is approaching a pre-selected maximum, a control circuit closes a valve in the vent line so as to block the discharge of air from the vessel and to create a backpressure that stops the receipt of further fluid.

U.S. Pat. No. 5,776,118, issued on Jul. 7, 1998 to Seifert et al., describes another collection and disposal system in which a collection vessel is connected for receiving waste fluids. The collection vessel is connected by a valve with a drain for draining the collected fluids. A fluid inlet is connected with an exterior water source to supply water through interconnected tubing to rinse waste residue from the collection vessel. A powdered reagent is received in a cup that is carried by a drawer to a position above the fluid mixing reservoir. A pump re-circulates the water through the reservoir to make the disinfectant fluid concentrate which is supplied to a venturi to be selectively entrained in the rinse water. U.S. Pat. No. 5,885,240, issued on Mar. 23, 1999 to the same inventor, describes a similar type of system.

U.S. Pat. No. 5,914,047, issued on Jun. 22, 1999 to G. R. Griffiths, teaches an on-site biohazardous waste collection and treatment system. The infectious fluid is treated by using a vacuum to draw in a disinfectant to be mixed with the biohazardous material. The requisite suction is created by peristaltic pump. U.S. Pat. No. 6,039,724, issued on Mar. 21, 2000 to the same inventor, describes a similar system.

Unfortunately, these systems utilize complex arrangements of mechanical pumps for the purpose of mixing the disinfectant with the biological fluid. In many circumstances, the pump itself must be repaired or cleaned so as to make the system suitable for future use. The use of various mechanical and electrical pumps further complicates the system and makes the system much more expensive. It is often difficult to specifically and accurately regulate the mixture of fluid with the disinfectant using such systems. Whenever such mechanical and electrical systems are employed, repair is frequently required. Under certain circumstances, the pumps and fluid lines must be primed before the pumping and mixing action can occur.

It is an object of the present invention to provide such a system which allows for the proper disposal of biological fluids.

It is another object of the present invention to provide such a system which reduces the cost associated with disposal.

It is a further object of the present invention to provide such a system which reduces liability caused by biological fluid spills.

It is a further object of the present invention to provide such a system which does not require the use of mechanical or electrical pumping apparatus.

It is a further object of the present invention to provide such a system which assures a proper dosing of the disinfectant with the biological fluid.

It is a further object of the present invention to provide such a system which automatically and inherently stops the mixing action and the pumping of disinfectant when the biological fluid supply is exhausted.

It is still another object of the present invention to provide such a system which reduces the complications associated with the cleaning of the mechanism.

These and other objects and advantages of the present invention will become apparent from a reading of the attached specification and appended claims.

BRIEF SUMMARY OF THE INVENTION

The present invention is a biological fluid disposal system comprising a water flow line, a biological fluid line in fluid communication with the water flow line, and a disinfectant line in fluid communication with the water flow line and the biological fluid line. The biological fluid line and the disinfectant line are connected with the water flow line such that a flow of water through the water flow line causes a suction action through the biological fluid line and the disinfectant line.

This effect is created by passing water flow through the water flow line so as to create a venturi effect therein. The biological fluid and the disinfectant are intimately mixed together through the biological fluid line prior to entering the water flow line.

A water inlet communicates with one end of the water flow line. An outlet is connected to the water flow line on an opposite end of the water flow line. The outlet serves to pass the mixed disinfectant, biological fluid and water toward a sewer.

The biological fluid line comprises a pipe which communicates with the water flow line. The disinfectant line is connected to this pipe at a distance from the water flow line and between an inlet of the pipe and the water flow line. A valve is connected to the pipe for limiting the rate of biological fluid flow through the biological fluid line. A suction line can extend outwardly of this pipe. It is connected to the valve. The suction line is suitable for insertion into a biological fluid container. The biological fluid container can have a supply of biological fluid therein. The suction line is positioned so as to removably extend below the top level of biological fluid within the biological fluid container. The disinfectant line comprises a pipe which communicates with the biological fluid line. A suction line extends outwardly of this pipe. The suction line is suitable for insertion into a disinfectant container. The disinfectant container can have a supply of disinfectant therein. The suction line has an inlet which extends into the disinfectant within the container. A metering valve is interconnected to this pipe for limiting the rate of disinfectant flow through the pipe.

A housing extends over the water flow line and the biological fluid line and the disinfectant line. The water flow line has an inlet and an outlet extending outwardly of the housing. The biological fluid line has an inlet positioned outwardly of the housing. The disinfectant line has an inlet extending outwardly of the housing.

The present invention is also a method of disposing of a biological fluid comprising the steps of: (1) connecting a biological fluid line to a disinfectant line such that one of the lines opens into the other line; (2) connecting the water flow line to an outlet of the other of the biological fluid line and the disinfectant line; (3) passing water through the water flow line across the outlet so as to cause a venturi effect to draw biological fluid and disinfectant through the respective biological fluid line and disinfectant line; (4) mixing the biological fluid and the disinfectant and the other of the biological fluid line and the disinfectant line; and (5) discharging the water and the mixed biological fluid and the disinfectant from the water flow line. The disinfectant line is connected to the biological fluid line between an inlet of the biological fluid line and the outlet. The inlet of the biological fluid line is inserted into a container of biological fluid. The inlet of the disinfectant line is inserted into a container of disinfectant. The rate of flow of disinfectant is controlled relative to the rate of flow of biological fluid.

DETAILED DESCRIPTION OF THE INVENTION

Figure 1:
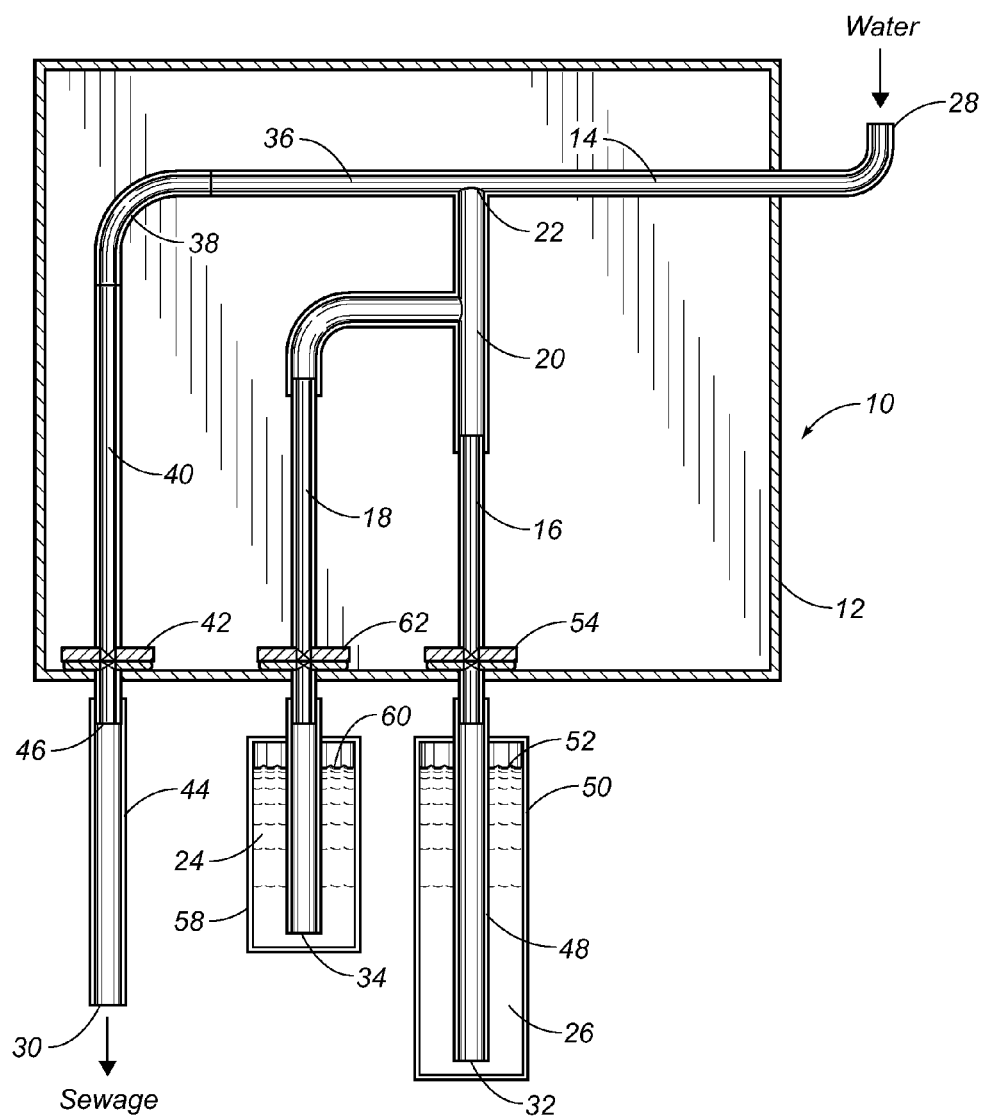
FIG. 1 is a cross-sectional view showing the biological fluid disposal system in accordance with the preferred embodiment of the present invention.

Referring to FIG. 1, there is shown at 10 a biological fluid disposal system in accordance with the teachings of the present invention. The biological fluid disposal system 10 includes a housing 12, a water flow line 14, a biological fluid line 16 and a disinfectant line 18. The biological fluid line 16 is in fluid communication with the water flow line 14. The disinfectant line 18 is in fluid communication with the biological fluid line 16 and with the water flow line 18. The biological fluid line 16 and the disinfectant line 18 are connected such that the biological fluid and disinfectant are mixed in pipe 20 and discharged into the water flow line 14 at outlet 22. The flow of water through the water flow line 14 across the outlet 22 creates a venturi effect so as to create a suction within the pipe 20 for drawing the disinfectant 24 through the disinfectant line 18 and for drawing the biological fluid 26 into and through the biological fluid line 16.

As can be seen in FIG. 1, housing 12 will extend around and over the water flow line 14, the biological fluid line 16, and the disinfectant line 18. The water flow line 14 has an inlet 28 which extends outwardly of the housing 12. The water flow line 14 also has an outlet 30 which extends outwardly of the housing 12. The biological fluid line 16 has an inlet 32 which extends outwardly of the housing 12. The disinfectant line 18 also has an inlet 34 which extends outwardly of the housing 12.

The water flow line 14 has its inlet 28 connected to a source of water pressure. The source of water pressure can be a hospital faucet, a gravity-fed source of water, or a supply of water pumped from a tank or other container. The water flow through the water flow line 14 should be sufficiently great so as to cause the venturi effect across the outlet 22. The water flow line 14 has a horizontal portion 36 connected by a curved coupling 38 to a vertical portion 40. A back wash valve 42 is connected to the vertical portion 40. A flexible hose (or other item) 44 can be connected to the terminal end 46 of the vertical portion 40 so as to allow the water flow line 14 to be connected to a drain and, eventually, to a sewer. The water flow line 14 is configured so as to deliver the water and the mixed disinfectant and biological fluid to the drain and into the sewage system. The back wash valve 42 can be suitably connected to a source of water pressure so that a reverse flow of water and disinfectant can be sent through the water flow line 14 for the cleaning of the system 10.

The biological fluid line 16 includes pipe 20 which communicates with the water flow line 14. The disinfectant line 18 is connected to the pipe 20 between the outlet 22 and the inlet 32. A suction line 48 is connected to the pipe 20 of the biological fluid line 16. As can be seen in FIG. 1, the suction line 48 is received within the interior of a biological fluid container 50. Biological fluid container 50 has a supply of biological fluid 26 therein. The inlet 32 of the biological fluid line 16 will open below the top level 52. When the requisite suction is created by the flow water across the outlet 22, the biological fluid 26 will be drawn into the inlet 32 and upwardly through the biological fluid line 16 prior to being mixed with the disinfectant 24 from the disinfectant line 18.

A valve 54 is connected along the biological fluid line 16 between the inlet 32 and the outlet 22. Valve 54 can control the rate of biological fluid flow through the biological fluid line 16. The valve 54 can be a simple metering valve which controls fluid flow rates.

Within the concept of the present invention, the biological fluid can be blood, blood products, body fluids, urine or mucus. The container 50 can be in the form of an open container which is transported from the surgical room to a disposal area. Alternatively, the container 50 can be a blood bag which is secured in a sealed manner to the inlet 32 of the biological fluid line 16.

The disinfectant line 18 has a pipe 56 which is connected to the pipe 20 of the biological fluid line 16. As such, the disinfectant 24 from a disinfectant container 58 is discharged into the pipe 20 for intimate mixing with the biological fluid 26 therein. The disinfectant line 18 has inlet 34 residing within the disinfectant container 58 at a location below the top level 60 of the disinfectant 24 within the container 58. A metering valve 62 is connected along the disinfectant line 18 so as to control the rate of disinfectant flow through the disinfectant line 18. The valves 54 and 62 of the respective biological fluid line 16 and the disinfectant line 18 can be suitably adjusted so that the proper mixture of the disinfectant 24 and biological fluid 26 can be obtained.

The disinfectant 24 will typically be of a formula and concentration sufficient upon contact, to reduce and eliminate the pathogenic agents present in the biological fluid 26. In the preferred form of the present invention, the chemical disinfectant is a chlorine-based compound in liquid form.

As can be seen in the present invention, the system 10 is a static system which does not require mechanical or electrical appliances. The venturi action of passing the flow of water across the outlet 22 will cause a proper mixing of the disinfectant 24 with the biological fluid 26. No complicated pumping mechanisms are required. The water inlet 28 can be simply connected to a source of water pressure. The outlet of the water flow line 14 can be simply inserted into a suitable drain so that the mixed and disinfected biological fluid can be discharged into a sewer. The arrangement of the components assures a proper mixture of disinfectant 24 and biological fluid 26 for decontamination. Cleaning of the system is very easy because of the lack of mechanical mechanisms.

An interesting feature of the present invention is that the system is its self-regulation. In any venturi-type system, fluids will flow in the direction of least resistance. When the supply of biological fluid 26 is exhausted from container 50, the inlet 32 will simply suck air therethrough. As a result, no disinfectant 24 will be drawn, at that time, from the container 58. As such, there is no need to monitor the system to shut off the system when the biological fluid supply is exhausted.

Figure 2:
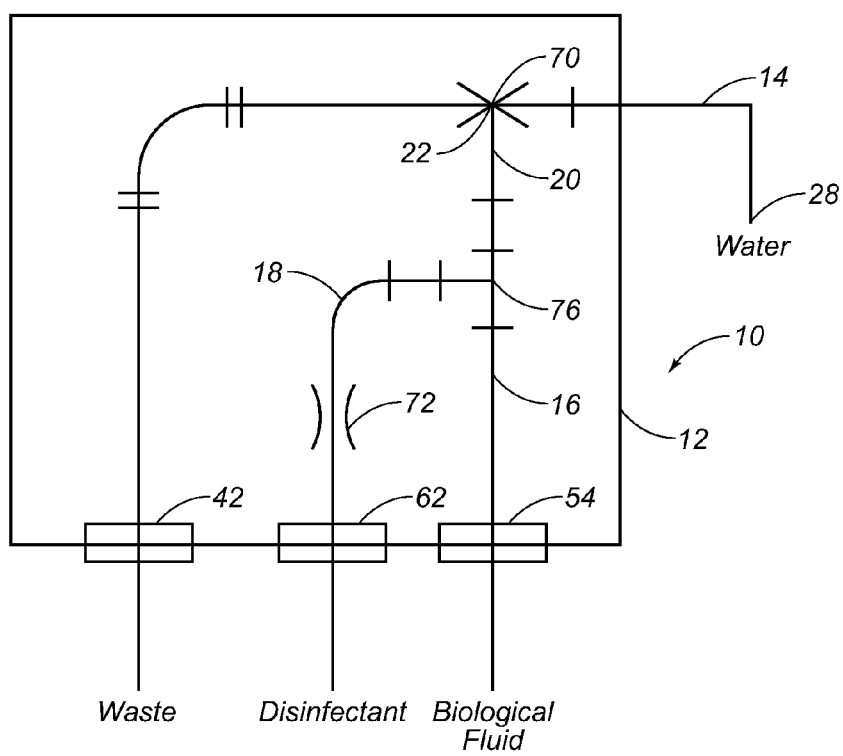
FIG. 2 is a diagrammatic illustration of the process used by the system of the present invention.

FIG. 2 is a diagrammatic illustration of the process of the present invention. As can be seen, water is introduced into inlet 28 under pressure. The water will flow through the water flow line 14 across venturi 70 so as to create the requisite suction on the biological fluid line 16. This suction will draw biological fluid through the biological fluid line 16 and will, simultaneously, draw the disinfectant through the orifice 72 associated with the disinfectant line 18. The rate of mixing of the disinfectant with the biological fluid is assured by the proper manipulation of the metering valves 54 and 62. The mixture of biological fluid and disinfectant will directly occur in the pipe 20 between the outlet 76 of the disinfectant line 18 and the outlet 22 of the biological fluid line 16. The mixture of the biological fluid and the disinfectant will flow into the water flow passing through the water flow line 14 in the area past the outlet 22. This mixed and decontaminated waste can then be discharged as waste into the sewer system. Each of the components can be safely secured in a sealed housing 12.

The foregoing disclosure and description of the invention is illustrative and explanatory thereof. Various details of the illustrated constructions or the steps of the described method can be changed within the scope of the appended claims without departing from the true spirit of the invention. The present invention should only be limited by the following claims and their legal equivalents.

I claim:

1. A biological fluid disposal system comprising:
   a housing;
   a water flow line having an inlet and an outlet extending outwardly of said housing;
   a biological fluid line in fluid communication with said water flow line, said biological fluid line having an inlet positioned outwardly of said housing; and
   a disinfectant line in fluid communication with said water flow line, said disinfectant line being in valveless fluid communication at a connection point with said biological fluid line within said housing, said disinfectant line having an inlet extending outwardly of said housing, said biological fluid line and said disinfectant line being connected to said water flow line such that solely a flow of water through said water flow line causes a suction action through said biological fluid line and said disinfectant line to draw a biological fluid line through said biological fluid line and draw a disinfectant through said disinfectant line so as to mix the disinfectant with the biological fluid prior to passing into said water flow line, said housing having no pumps therein, the suction action through said disinfectant line being dependent upon flow of said biological fluid.

2. The system of claim 1, said water flow line having an inlet means and an outlet means, said inlet means for passing a water flow through said water flow line, said outlet means for releasing a mixture of the biological fluid and the water and the disinfectant from said water flow line.

3. The system of claim 1, further comprising:
   a water inlet communicating with one end of said water flow line; and
   an outlet means connected to said water flow line on an opposite end of said water flow line, said outlet means for passing a flow of liquid from said water flow line to a sewer.

4. The system of claim 1, said biological fluid line comprising:
   a pipe communicating with said water flow line and having a connection to said disinfectant line at a distance from said water flow line and between an inlet of said pipe and said water flow line, the biological fluid mixing with the disinfectant in said pipe.

5. The system of claim 4, further comprising:
a valve means connected to said pipe between said inlet of said pipe and said connection to said disinfectant line, said valve means for limiting a rate of biological fluid flow through said biological fluid line.

6. The system of claim 1, further comprising:
a biological fluid container having a supply of biological fluid therein, said supply of biological fluid having a top level within said biological fluid container, said inlet of said biological fluid line removably extending so as to have said inlet positioned below said top level, said supply of biological fluid being substantially blood.

7. The system of claim 1, said disinfectant line comprising:
a pipe in valveless communication with said biological fluid line at a connection point within said housing, said inlet of said disinfectant line extending outwardly of said pipe, said inlet of said disinfectant line suitable for insertion into a disinfectant container.

8. The system of claim 7, the disinfectant container having a supply of disinfectant therein, said supply of disinfectant having atop level within the disinfectant container, said inlet of said disinfectant line removably extending below said top level.

9. A biological fluid disposal system comprising:
a water flow line;
a biological fluid line in fluid communication with said water flow line;
a disinfectant line having a valveless connection at a connection point to said biological fluid line, said disinfectant line being in fluid communication with said biological fluid line between said water flow line and an inlet of said biological fluid line;
a venturi means connected to said water flow line for creating a suction force so as to draw a biological fluid through said biological fluid line and to draw a disinfectant through said disinfectant line so as to mix intimately together in said biological fluid line prior to passing as a mixture into said water flow line, the biological fluid line being substantially blood.

10. The system of claim 9, said venturi means comprising:
a source of water pressure connected to said water flow line such that solely a water flow across an opening of at least one of said biological fluid line and said disinfectant line creates said suction force.

11. The system of claim 9, further comprising:
a sewer interconnected to an outlet of said water flow line.

12. The system of claim 9, further comprising:
a biological fluid container having a supply of the biological fluid therein, said supply of the biological fluid having a top level within said biological fluid container, said biological fluid line having an inlet below said top level; and
a disinfectant container having a supply of the disinfectant therein, said supply of the disinfectant having a top level within said disinfectant container, said disinfectant line having an inlet below said top level of said supply of the disinfectant.

13. A method of disposing of a biological fluid comprising:
connecting a biological fluid line in valveless relation to a disinfectant line at a connection point such that one of said biological fluid line and said disinfectant line opens into the other of said biological fluid line and said disinfectant line;
connecting a water flow line to an outlet of the other of said biological fluid line and said disinfectant line;
passing water through said water flow line across said outlet so as to cause a venturi effect to solely draw a biological fluid and a disinfectant through the respective biological fluid line and disinfectant line, the biological fluid line being substantially blood, wherein flow of said biological fluid through the biological fluid line coincides in time with flow of said disinfectant through the disinfectant line;
mixing the biological fluid and the disinfectant in the other of said biological fluid line and said disinfectant line; and
discharging the water and the mixed biological fluid and disinfectant from said water flow line.

14. The method of claim 13, said step of connecting said biological fluid line to said disinfectant line comprising:
connecting said disinfectant line to said biological fluid line between an inlet of said biological fluid line and said outlet.

15. The method of claim 13, further comprising:
inserting an inlet of said biological fluid line into a container of the biological fluid; and
inserting an inlet of said disinfectant line into a container of the disinfectant.

\* \* \* \* \*